US010149795B2

(12) United States Patent
Andersen et al.

(10) Patent No.: US 10,149,795 B2
(45) Date of Patent: Dec. 11, 2018

(54) METHOD AND SYSTEM FOR BEHAVIORAL TRAINING TO IMPROVE SIGHT (71) Applicant: The Regents of the University of California, Oakland, CA (US)

(72) Inventors: George J. Andersen, Riverside, CA (US); Denton J. DeLoss, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/447,041

(22) Filed: Mar. 1, 2017

(65) Prior Publication Data

US 2017/0252257 A1  Sep. 7, 2017

Related U.S. Application Data

(60) Provisional application No. 62/302,039, filed on Mar. 1, 2016.

(51) Int. Cl.
| | |
|---|---|
| *A61H 5/00* | (2006.01) |
| *A61B 3/00* | (2006.01) |
| *A61B 3/032* | (2006.01) |
| *A61B 3/11* | (2006.01) |
| *A61B 3/02* | (2006.01) |

(52) U.S. Cl.
CPC .............. *A61H 5/00* (2013.01); *A61B 3/0025* (2013.01); *A61B 3/0033* (2013.01); *A61B 3/0041* (2013.01); *A61B 3/0091* (2013.01); *A61B 3/022* (2013.01); *A61B 3/032* (2013.01); *A61B 3/112* (2013.01); *A61H 2201/5007* (2013.01); *A61H 2201/5043* (2013.01)

(58) Field of Classification Search
CPC .......... A61H 5/00; A61B 3/032; A61B 3/024; A61B 3/02; A61B 3/0033
USPC .......................... 351/203, 222, 223, 237, 246
See application file for complete search history.

(56) References Cited

U.S. PATENT DOCUMENTS

| | | | | |
|---|---|---|---|---|
| 2010/0134758 A1* | 6/2010 | Petignaud | ................ | A61B 3/02 351/203 |
| 2011/0001924 A1* | 1/2011 | Giraudet | ................. | A61B 5/16 351/203 |

* cited by examiner

Primary Examiner — Mohammed Hasan
(74) Attorney, Agent, or Firm — Ivan M. Posey, Esq.

(57) ABSTRACT

A perceptual-learning system and method is used to improve age-related declines in contrast sensitivity. The system and method comprises a processor and monitor, and a first set of instructions executable on the processor configured to familiarize subjects with the system. A second set of instructions are executable on the processor configured for training the subjects.

10 Claims, 10 Drawing Sheets

METHOD AND SYSTEM FOR BEHAVIORAL TRAINING TO IMPROVE SIGHT

CROSS-REFERENCE TO RELATED APPLICATIONS

This application claims the benefit of U.S. Provisional Patent Application No. 62/302,039, entitled "Low Contrast Training Protocol to Improve Vision", filed Mar. 1, 2016, the contents of which are incorporated herein by reference in their entirety.

STATEMENT REGARDING FEDERALLY SPONSORED RESEARCH OR DEVELOPMENT

This invention was made with Government support under Grant No. AG031941, awarded by the National Institutes of Health. The Government has certain rights in this invention.

FIELD OF THE INVENTION

The invention relates to a method and system for behavioral training to improve sight. More specifically, a perceptual-learning system and method is used to improve age-related declines in contrast sensitivity.

BACKGROUND

Researchers estimate that between 2000 and 2050, the number of older individuals (over the age of 65 years) in the United States will increase 135%, whereas the population under age 65 will increase only 32% (Wiener & Tilly, 2002). The number of individuals living to an advanced age (age 85 and older)—a group likely to need health- and long-term care services—is projected to increase by a staggering 350%. These percentages trans-late to an estimated increase of 47 million individuals age 65 and older (Wiener & Tilly, 2002). An important issue will be to develop strategies to address the health needs of this ever-growing sector of the population.

It is well documented in the literature that cognition significantly declines as people age. This decline includes changes in executive function, fluid intelligence and working memory, inhibitory control and attention, and language processing (see Craik & Salthouse, 2007, for a detailed review). In addition to cognitive declines, there are significant age-related declines in vision and visual processing that influence the health and well-being of an aging population. These declines have been identified as a major factor in the incidence of falls among the elderly (Lord, Smith, & Menant, 2010). In addition, age-related declines in vision have been associated with increased risk of motor-vehicle crashes (Owsley et al., 1998; Owsley, Stalvey, Wells, & Sloane, 1999); in fact, the crash risk for drivers over the age of 75 exceeds that for novice young drivers (Evans, 2004). The types of crashes that occur change with driver age: Compared with younger drivers, older drivers have more collisions with other moving vehicles and less single-vehicle or speed-related crashes (Langford & Koppel, 2006), which suggests that there are specific declines in visual function with age.

Given the health outcomes of age-related declines in vision, an important question is what aspects of vision and visual processing decline with age. A substantial corpus of research (see Owsley, 2011, and Andersen, 2012, for reviews) has shown age-related declines in a vast range of visual functions, including contrast sensitivity. (Richards, 1977), orientation discrimination (Betts, Sekuler, & Bennett, 2007), visual acuity (Sekuler, Owsley, & Hutman, 1982), motion perception (Bennett, Sekuler, & Sekuler, 2007), form perception (Roudaia, Bennett, & Sekuler, 2008), and optic flow (Atchley & Andersen, 1998). While these age-related declines in visual function could be due to optical, retinal, cortical, or pathological changes, there is substantial evidence suggesting a corti-cal locus (Spear, 1993). Specifically, studies have suggested that these changes may be due to decreased cortical inhibition in visual cortex (Schmolesky, Wang, Pu, & Leventhal, 2000).

Of all these age-related declines in vision and visual processing, the decline in contrast sensitivity is one of the most pronounced. Declines in contrast sensitivity significantly affect visual function, including the ability to detect and resolve detail (e.g., Owsley, Sekuler, & Siemsen, 1983), process motion information important for balance (Sundermier, Woollacott, Jensen, & Moore, 1996), and process information when driving (Liutkeviciene, Cebatoriene, Liutkeviciene, Jasinskas, & Zaliu-niene, 2013). Declines in contrast sensitivity have also been found to be related to the likelihood of falls among older adults (Lord, Clark, & Webster, 1991). Contrast-sensitivity declines are most apparent at high spatial frequencies, and while it has been suggested that this decrease in contrast sensitivity is primarily due to optical factors, the decline in contrast sensitivity for moving stimuli may have a significant neural component (Burton, Owsley, & Sloane, 1993).

SUMMARY OF THE INVENTION

According to a preferred embodiment, a computerized system for improving sight, comprises: a processor; a monitor; a first set of instructions executable on the processor configured to familiarize subjects with the system, said first set of instructions including: instructions for presenting a fixation point in the center of the monitor, alternating between black and white, instructions for presenting a Gabor patch on the monitor, instructions for presenting a second stimulus on the monitor, instructions for receiving input from the subjects on how the second stimulus is oriented; and a second set of instructions executable on the processor configured for training the subjects, said second set of instructions including: instructions for presenting Gabor patches embedded in additive Gaussian noise on the monitor, instructions for increasing the standard deviation of the Gaussian distribution, and instructions for receiving input from the subjects on how the Gabor patches are oriented.

According to another preferred embodiment, a method for improving sight, comprises: familiarizing subjects by: presenting a fixation point in the center of the monitor, alternating between black and white, presenting a Gabor patch on the monitor, presenting a second stimulus on the monitor, receiving input from the subjects on how the second stimulus is oriented; and training the subjects by: presenting Gabor patches embedded in additive Gaussian noise on the monitor, increasing the standard deviation of the Gaussian distribution, and receiving input from the subjects on how the Gabor patches are oriented.

BRIEF DESCRIPTION OF THE DRAWINGS

These and other features, aspects and advantages of the present invention will become better understood with regard to the following description, appended claims, and accompanying drawings where:

DETAILED DESCRIPTION

For illustrative purposes, the present invention is embodied in the apparatus and method generally shown and described herein with reference to FIG. 1 through FIG. 10. It will be appreciated that the apparatus may vary as to configuration and as to details of the parts, and that the method may vary as to the specific steps and sequence, without departing from the basic concepts as disclosed herein.

The present invention overcomes the limitations of the prior art by providing a method and system for behavioral training to improve sight. Perceptual learning refers to improved visual performance as a result of repeated exposure to stimuli usually at or near an individual's perceptual threshold. A number of perceptual-learning studies have shown that perceptual improvements are specific to the trained stimuli and do not transfer to other, nontrained stimuli or tasks. Specificity has been shown for orientation, task difficulty, the presence or absence of external noise, and location in the visual field, as well as a combination of these factors. This specificity is an important issue to examine if perceptual-learning paradigms are to be used to counteract age-related declines in vision. For these reasons, it is element in the present invention to examine specificity for the trained stimuli, as well as the possibility of transfer to other real-world tasks.

In the past decade, a number of studies have examined perceptual learning in older individuals. Only one of these studies found complete specificity to an untrained retinal location, while numerous other studies found partial to complete transfer to an untrained task, orientation, or stimulus. This decreased specificity may be due to decreased neural inhibition, as well as decreased orientation and direction of neuronal selectivity. Because of this decreased selectivity, broader ranges of neurons may be recruited during training, allowing for transfer not typically seen in younger adults. Although these age-related decreases in selectivity may make fine discrimination more difficult, they may result in a greater benefit from perceptual learning because of decreased specificity and greater generality for trained tasks and stimuli.

The present study assessed whether perceptual learning could be used as a possible intervention to counter-act age-related declines in contrast sensitivity. Younger and older subjects performed an orientation-discrimination task using sine-wave gratings that varied in contrast. The developer of the system and method described herein assessed whether training improved performance for targets at a specific orientation, transferred to targets at an untrained orientation, and transferred to other tasks (e.g., near- and far-acuity tests). While previous studies have used contrast-training paradigms to improve vision in middle-age individuals), the presently described system is the first to examine the use of perceptual learning to improve vision in adults 65 years of age and older. In addition, it is possible that improved performance could be due to changes in retinal illuminance—the amount of light reaching the retina. To examine this issue, pupil diameter was measured. If improved performance is due to increased light reaching the retina (pupil dilation), then retinal illuminance should be correlated with improvements in performance following training.

System and Method Used on Test Subjects

Sixteen younger adults (mean age=22.43 years, SD=1.16) from the University of California, Riverside (8 male and 8 female) and 16 older adults (mean age=71.23 years, SD=5.85) from the surrounding community (8 male and 8 female) participated in the study. The sample size was determined on the basis of pilot studies and previous research demonstrating an effect of training in older and younger adults. The sample size for each age group was comparable with sample sizes in other studies investigating the effects of perceptual learning. Subjects were naive to the purpose of the study, and all had normal or corrected-to-normal visual acuity.

TABLE 1

Demographic Information and Results From Cognitive and Perceptual Tests Administered Prior to the Start of the Study

| | Younger adults | | Older adults | |
|---|---|---|---|---|
| Variable | M | SD | M | SD |
| Age (years) | 22.43 | 1.16 | 71.23 | 5.85 |
| Education (years) | 15.00 | 0.88 | 15.15 | 2.34 |
| Log contrast sensitivity | 1.37 | 0.43 | 1.29 | 0.19 |
| Visual acuity (LogMAR units)[a] | −0.02 | 0.09 | 0.09 | 0.12 |
| WAIS: Digit Span Forward | 10.79 | 1.72 | 9.85 | 1.63 |
| WAIS: Digit Span Backward | 7.71 | 1.94 | 6.23 | 2.39 |
| WAIS: Matrix Reasoning[a] | 20.29 | 2.67 | 16.92 | 4.19 |

Note:
Contrast sensitivity was measured using the Pelli Robson Test (Pelli, Robson, & Wilkins, 1988).
LogMAR = logarithm of the minimum angle of resolution.
WAIS = Wechsler Adult Intelligence Scale-third edition (Wechsler, 1997).
[a]For these tests, the difference between groups was significant (p < .05).

All subjects were screened using an array of cognitive and perceptual tests. This procedure ensured that the older group did not exhibit any early or atypical cognitive decline (e.g., Alzheimer's disease) that could influence the results of the study. Demographic information for the subjects is presented in Table 1. One-way analyses of variance revealed that prior to training, there were significant differences between the two age groups in acuity and on the Matrix Reasoning subtest of the third edition of the Wechsler Adult Intelligence Scale (Wechsler, 1997; Fs≤2.5, ps>0.05). While the older group's performance was significantly different from that of the younger group on Matrix Reasoning, their score was well above the age norm found in previous research (Ardila, 2007). Subjects were also screened for eye disease and neurological disorders.

Apparatus

Figure 1:
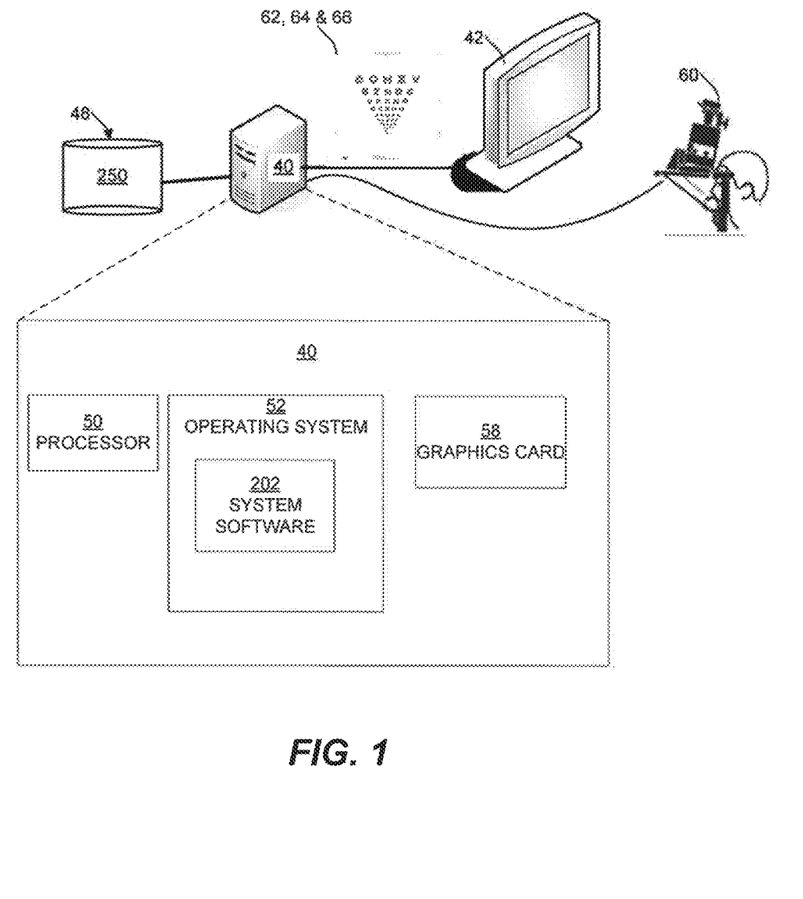
FIG. 1 is a diagrammatic representation an apparatus on which the system may operate according to one embodiment.

With reference to FIG. 1, a diagrammatic representation an apparatus on which the system may operate is shown according to one embodiment. Stimuli may be presented on a 21-inch. CRT monitor 42 (Viewsonic P225F) at a resolution of 1,024×768 pixels; the monitor 42 may have a refresh rate of 100 Hz (noninterlaced) and a mean luminance value of 53.82 cd/m2. Stimuli were generated on a computer 40, which may comprise, for example, Dell Vostro 430 PC equipped with a processor 50 that may comprise an Intel Core i5 750 processor using the Windows XP (Service Pack 3) operating system 52. A GeForce GTS 240 graphics card 58 (NVIDIA, Santa Clara, Calif.) may be used along with a Bits++ system (Cambridge Research Systems, Rochester, Kent, United Kingdom) to achieve 14-bit gray scale (16,384 gray-scale levels).

The system software 202 may comprise one or more sets of instructions executable on the processor 52 written in MATLAB (The MathWorks, Natick, Mass.); Psychophysics Toolbox extensions were also utilized (Brainard, 1997; Pelli, 1997). The monitor may be calibrated using a ColorCal2 colorimeter (Cambridge Research Systems). Gamma correction was performed through linearization of the color lookup table.

Pupil size was measured on testing days using an EyeLink 1000 Tower Mount (SR Research, Ottawa, Ontario, Canada) 60; the subjects' head position may also stabilized with this device. The subjects' far acuity may be measured using the 2000 Series Revised ETDRS Chart 2 (Precision Vision, La Salle, Ill.) 62 at a distance of 3 m. The subjects' near acuity was measured using the 2000 series New ETDRS Chart 3 64 at a distance of 40 cm. Contrast sensitivity was measured using the Pelli-Robson Contrast Sensitivity Chart (Precision Vision) 66.

Stimuli and Procedure

Figure 2:
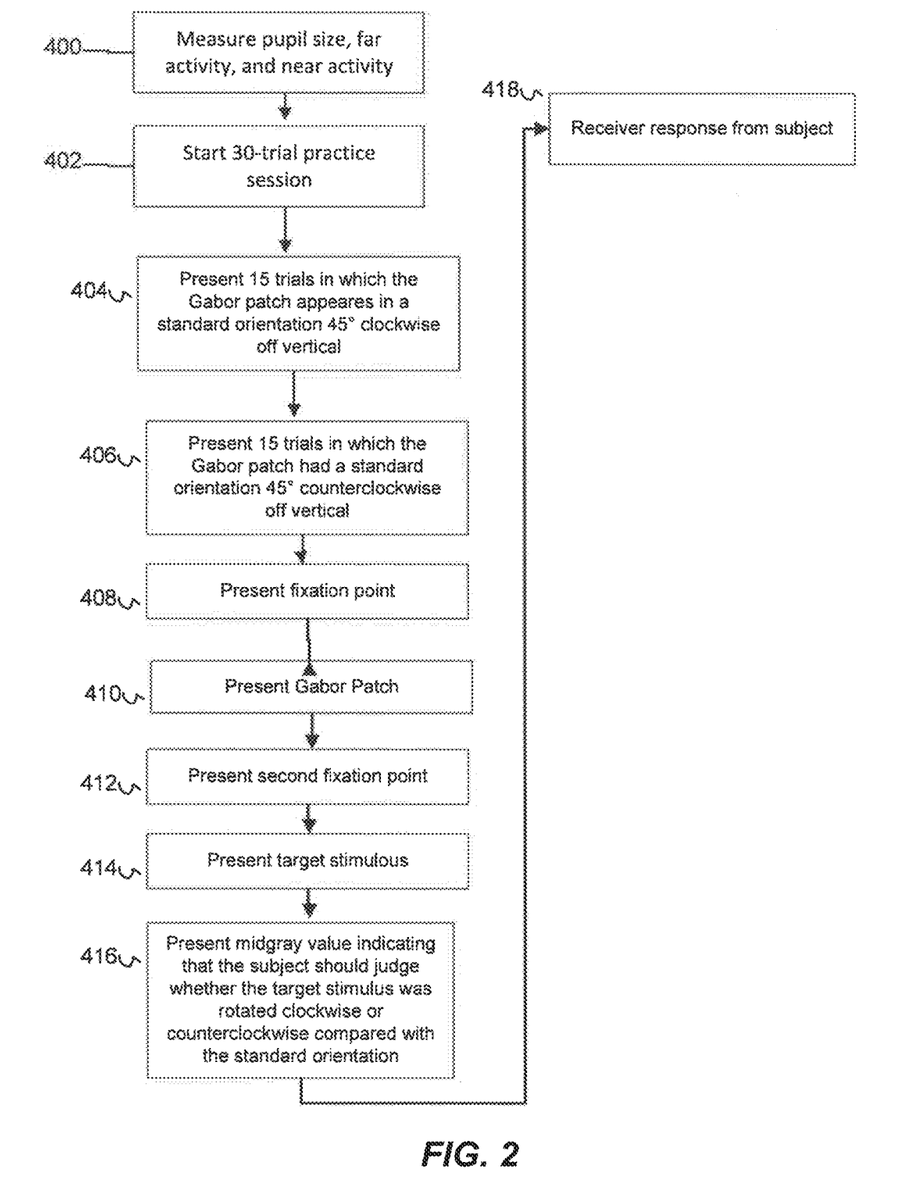
FIG. 2 is a flow diagram illustrating steps in a stimuli method performed by the system and software according to the embodiment of FIG. 1.

With reference to FIG. 2, a flow diagram illustrates steps in a stimuli method performed by the system and software according to the embodiment of FIG. 1. After the above-cited measurements are taken, step 402, in the test, the procedure comprised 1.5 hours per day of testing and training over 7 days. Subjects were required to complete the study within 3 weeks of their first testing session. Stimuli were viewed binocularly on the monitor 42 at a distance of 94 cm. Corrective lenses normally worn by the subjects were allowed during the experiment. All stimuli were viewed through a plano-convex glass collimation lens (45.7 cm diameter) with a 19% magnification factor to minimize any age-related differences in accommodative focus. The size of the stimuli was corrected to account for this magnification factor. The experiment was run in a darkened room; the only light source was the monitor. Stimuli were Gabor patches presented at 1.5 cycles per degree of visual angle (0.65° standard deviation of the Gaussian mask), and the phase of the Gabor was randomized ±180° on each trial.

Familiarization Task

Figure 3:
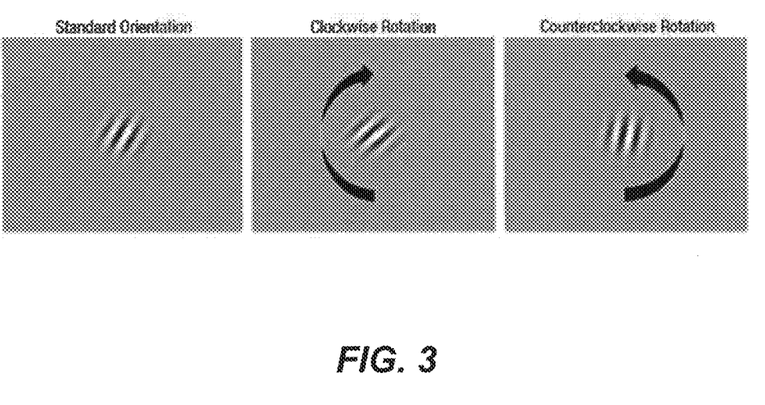
FIG. 3 is a diagram screen of images from the system that are presented in the task presented by the system.

On the first day of the study, before the method began, all subjects were given a 30-trial practice session to familiarize them with the task, step 402. With reference to FIG. 3, screen images from the system are presented showing the task presented by the system. In each trial, subjects saw a Gabor patch at one of two standard orientations—25° clockwise (shown here) or 25° counterclockwise for training and testing trials, 45° clockwise or 45° counterclockwise for familiarization trials. After this Gabor patch disappeared, subjects saw a second stimulus and had to judge whether it was rotated clockwise or counterclockwise in comparison with the standard orientation (the examples shown here are rotated 15° clockwise and counterclockwise off the standard orientation, respectively).

The practice trials may be presented without Gaussian noise. Subjects completed 15 trials in which the Gabor patch appeared in a standard orientation 45° clockwise off vertical, step 404, and 15 trials in which the Gabor patch had a standard orientation 45° counterclockwise off vertical, step 406. At the beginning of each trial, subjects were presented with a fixation point in the center of the display for 1,600 ms, step 408. This fixation point alternated between black and white every 400 ms, to attract attention. A Gabor patch then appeared at one of the two standard orientations for 100 ms, step 410. A second fixation point then appeared for 1,200 ms, alternating between black and white every 300 ms, step 412, followed by the target stimulus for 100 ms, step 414. During this phase, the target was rotated either 25° clockwise or 25° counterclockwise away from the standard orientation. After the target disappeared, the screen assumed a uniform midgray value indicating that the subject should judge whether the target stimulus was rotated clockwise or counterclockwise compared with the standard orientation, step 416. FIG. 3 is a series of exemplary screen shots.

In step 418, responses are made by the subject using the left and right arrow keys on the keyboard. Audio feedback was provided on each trial to indicate whether the subject was correct. Subjects were then prompted to "press any key to continue" to begin the next trial. During the familiarization task, subjects were instructed to get at least one trial incorrect to familiarize themselves with the corresponding auditory feedback.

Testing

Figure 4:
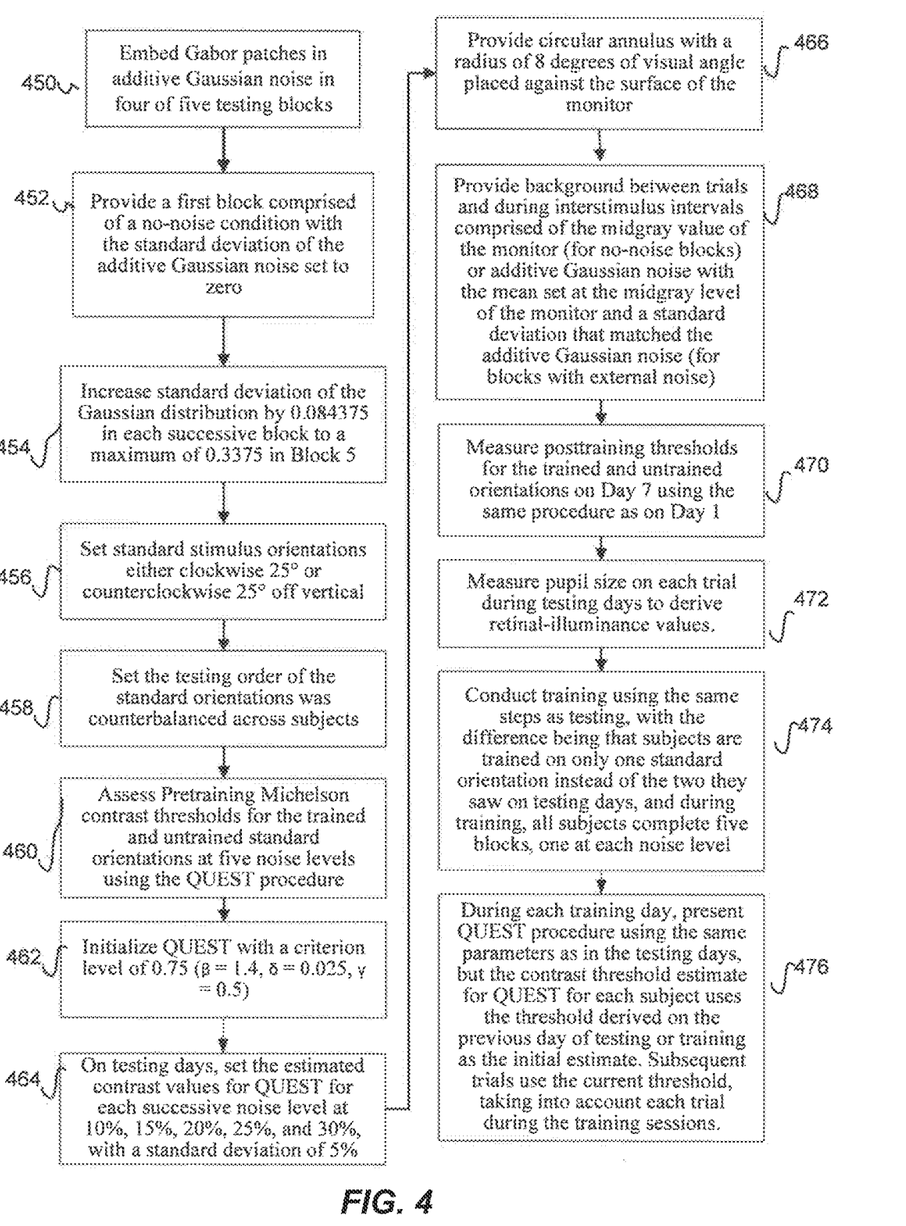
FIG. 4 is a flow diagram illustrating steps performed by the system for testing according to one embodiment.

With reference to FIG. 4, a flow diagram illustrates steps performed by the system for testing according to one embodiment. In an actual test, orientation-discrimination thresholds were tested during the first and last days (Days 1 and 7). During testing, the Gabor patches were embedded in additive Gaussian noise in four of the five testing blocks, step 450. The first block comprised a no-noise condition with the standard deviation of the additive Gaussian noise set to zero, step 452; the standard deviation of the Gaussian distribution was then increased by 0.084375 in each successive block to a maximum of 0.3375 in Block 5, step 454.

Figure 5:
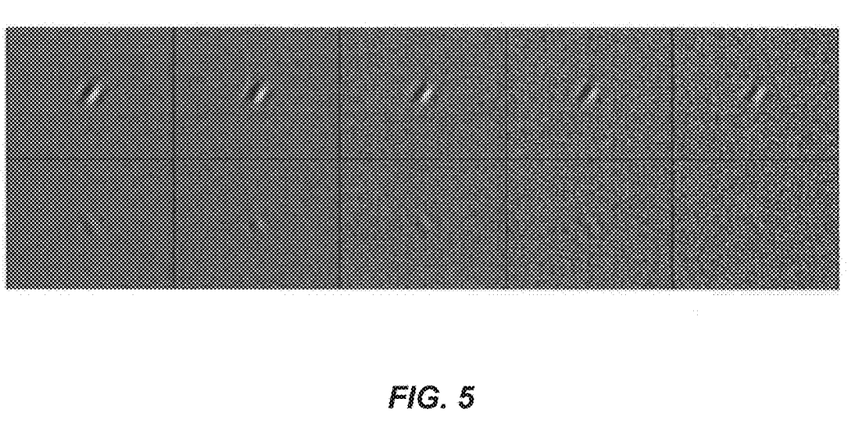
FIG. 5 is a diagram showing example of the stimuli according to one embodiment.

Standard stimulus orientations were either clockwise 25° or counterclockwise 25° off vertical, step 456. With reference to FIG. 5, an example of the stimuli is shown. In the example in FIG. 5, in each trial, the system presented a Gabor patch at one of two standard orientations-25° clockwise (shown here) or 25° counterclockwise for training and testing trials, 45° clockwise or 45° counterclockwise for familiarization trials. After this Gabor patch disappeared, subjects saw a second stimulus and had to judge whether it was rotated clockwise or counterclockwise in comparison with the standard orientation (the examples shown here are rotated 15° clockwise and counterclockwise off the standard orientation, respectively).

With reference back to FIG. 4, the testing order of the standard orientations was counterbalanced across subjects, step 458. These two orientations were chosen on the basis of previous research demonstrating that improvements in orientation sensitivity begin to degrade when the stimulus is rotated approximately 40° away from the trained orientation. These two specific standard orientations were chosen because they are 50° offset from one another.

During Days 1 and 7, pretraining Michelson contrast thresholds for the trained and untrained standard orientations were assessed at five noise levels using the QUEST procedure (Watson & Pelli, 1983), step 460. QUEST was initialized with a criterion level of 0.75 ($\beta=1.4$, $\delta=0.025$, $\gamma=0.5$). On testing days, the estimated contrast values for QUEST for each successive noise level were 10%, 15%, 20%, 25%, and 30%, with a standard deviation of 5%, step 464. Subjects completed 60 trials at each noise level during testing. All stimuli were viewed through a circular annulus with a radius of 8 degrees of visual angle that was placed against the surface of the monitor, step 466. The annulus removed any edge cues that may have been used in the orientation-discrimination task. The background between trials and during interstimulus intervals comprised the midgray value of the monitor (for no-noise blocks) or additive Gaussian noise with the mean set at the midgray level of the monitor and a standard deviation that matched the additive Gaussian noise (for blocks with external noise), step 468.

Trials progressed in the same fashion as in the familiarization task. The orientation offset was fixed at 15° on all test trials. Posttraining thresholds for the trained and untrained orientations were measured on Day 7 using the same procedure as on Day 1, step 470. Pupil size was also measured on each trial during testing days to derive retinal-illuminance values, step 472.

Training

Training occurred on Days 2 through 6 using the same stimuli and a similar procedure as in the testing phase, with the key difference being that subjects were trained on only one standard orientation instead of the two they saw on testing days. During training, all subjects completed five blocks, one at each noise level, step 474. There were 150 trials per block, and subjects were allowed to take a short break after each block. During each training day, the QUEST procedure was run using the same parameters as during the testing days, but with one modification. The contrast threshold estimate for QUEST for each subject used the threshold derived on the previous day of testing or training as the initial estimate. Subsequent trials used the current threshold, taking into account each trial during the training sessions. Using this method, subjects were constantly trained at their threshold (75% correct) during each training day. This allowed training to be constantly optimized for any improvement that occurred between or within testing or training sessions. All subjects received 750 training trials per day, for a total of 3,750 training trials over the course of the experiment.

Results

Threshold Analysis

Figure 6:
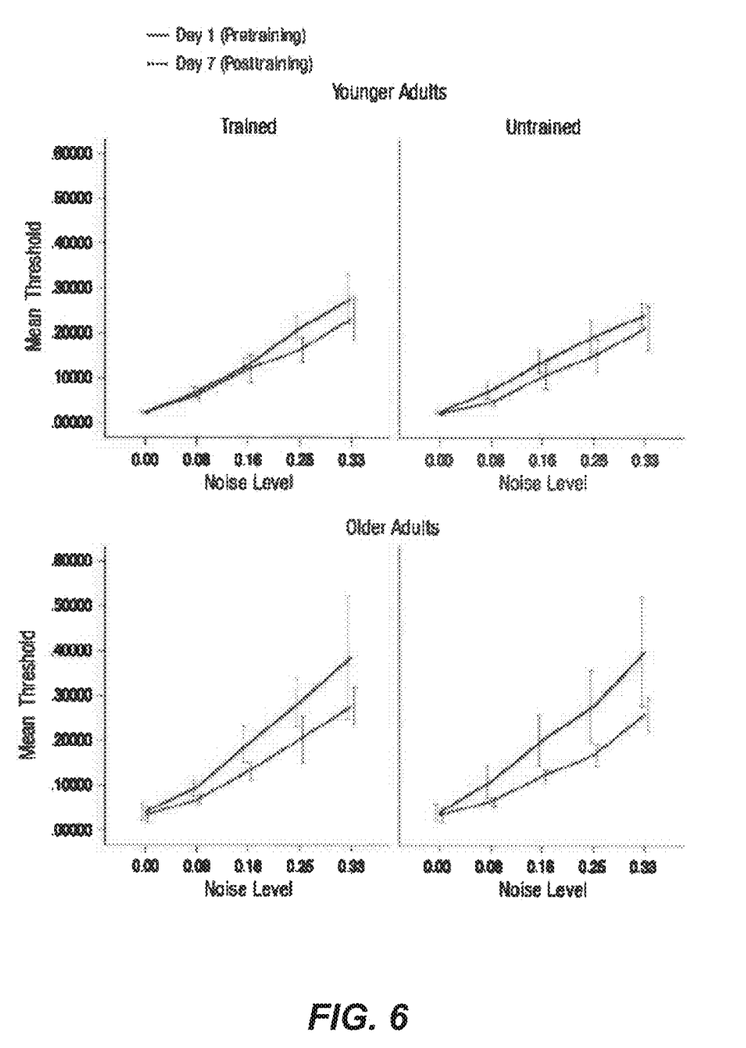
FIG. 6 is a graph that illustrates the mean Michelson contrast thresholds for older and younger adults shown as a function of noise level.

A 2 (testing day: pretraining, posttraining)×5 (noise level: 0-4)×2 (age group: older, younger)×2 (orientation: trained, untrained) mixed repeated measures analysis of variance was conducted on the thresholds obtained on the testing days. Two older individuals and three younger individuals had to be removed from the analysis, as QUEST was not able to converge on a stable threshold estimate in at least one of the conditions before or after training. Results revealed a significant effect of testing day, $R(1, 25)=30.696$, $p<0.001$, $r_p^2=0.551$, which indicates that there was a significant improvement in perceptual thresholds after training. A significant Testing Day×Age Group interaction was also found, $R(1, 25)=6.583$, $p=0.017$, $rp\ 2=0.208$: Compared with younger adults, older adults showed a greater performance improvement after training, as shown in FIG. 6. There was a significant difference in performance between older and younger adults prior to training, $R(1, 25)=8.314$, $p=0.008$, $r_p^2=0.250$. However, after training, this effect of age was no longer significant, $R(1, 25)=3.996$, $p=0.057$, $r_p^2=0.138$; performance for older and younger subjects was similar following training.

There was also a significant effect of noise level, $R(4, 100)=198.463$, $p<0.001$, $r_p^2=0.888$. As expected, as the level of external noise increased, so did subjects' contrast threshold. A significant Noise Level×Age Group interaction was also found, $R(4, 100)=4.209$, $p=0.035$, $r_p^2=0.144$. Older individuals showed lower tolerance to external noise, as exhibited by higher thresholds in the high-noise conditions (Blocks 4 and 5), both before and after training. There was also a significant Testing Day×Noise Level×Age Group effect, $R(4, 100)=2.506$, $p=0.047$, $r_p^2=0.091$. Older adults exhibited greater reductions in thresholds in the high-noise conditions, compared with younger adults.

A possible factor that might account for the observed learning is that improvements in performance are a result of repeated testing with the stimuli and practice with the task. To examine this possibility, the change in threshold between Days 1 and 2 was analyzed. The main effect of day was not significant for younger subjects, $R(1, 13)=2.04$, $p=0.177$, $r_p^2=0.135$, or for older subjects, $R(1, 12)=3.23$, $p=0.098$, $rp\ 2=0.212$, which suggests that the improved performance over the full range of training was not the result of repeated testing with the stimuli or task practice.

With reference to FIG. 6, a graph illustrates the mean Michelson contrast thresholds for older and younger adults shown as a function of noise level (values indicate the standard deviation of the Gaussian distribution) and testing day. Results are shown separately for trained and untrained orientations of the stimuli. Error bars indicate 95% confidence intervals.

Retinal-Illuminance Analysis

Figure 7:
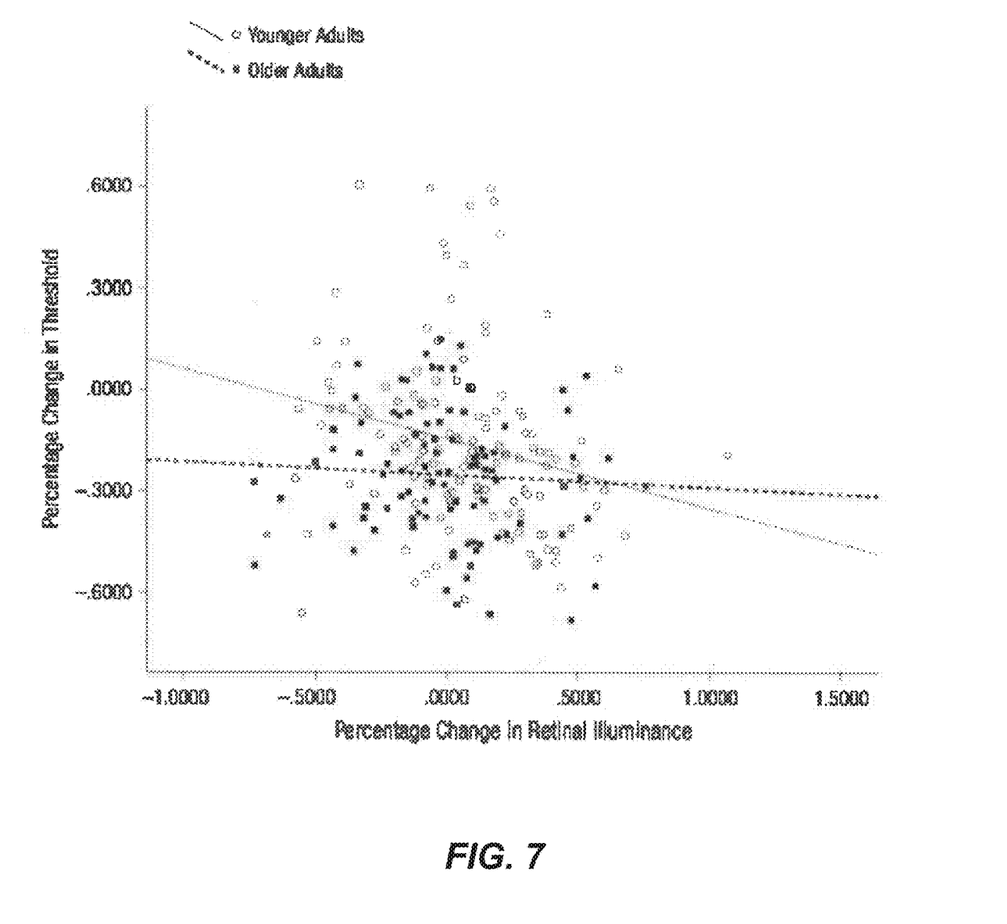
FIG. 7 is a scatter plot showing the percentage change in threshold as a function of the percentage change in retinal illuminance, separately for older and younger subjects.

To examine whether a change in pupil size was correlated with the change in threshold, pupil-size measurements were taken during each stimulus presentation, which were then converted into Trolands, the conventional unit of retinal illuminance. Percentage-change scores from before to after training for retinal illuminance and contrast thresholds were calculated. Any change greater than ±2.5 standard deviations was excluded from the analysis. All reported p values are one-tailed because it was hypothesized that letting more light into subjects' retinas would cause an improvement in performance for low-contrast stimuli, particularly in older individuals who have decreased retinal illuminance. Overall, there was a significant correlation between the percentage change in threshold and percentage change in retinal illuminance after training, $r(224)=-0.134$, $p=0.019$. However, further analysis indicated that this correlation was driven primarily by younger adults. When the data were split by age group, younger individuals continued to show a significant correlation, $r(122)=-0.228$, $p=0.004$, while older individuals showed no significant correlation, $r(102)=-0.059$, $p=0.276$, as shown in FIG. 7, which is a scatter plot showing the percentage change in threshold as a function of the percentage change in retinal illuminance, separately for older and younger subjects. Each point represents a single measurement at one of the five noise levels. The lines indicate the best-fitting linear trend for each age group.

Previous research has shown that pupil size can alter the retinal-modulation transfer function, which might enhance low and high spatial frequencies of the external noise and subsequently affect learning. To examine this issue, the testers correlated, between pretraining test and posttraining test, the change in pupil size with the change in contrast thresholds. The correlation was significant for younger adults, $r(122)=-0.36$, $p<0.001$, as well as for older adults, $r(102)=-0.18$, $p=0.035$. However, this accounted for only 13% of the variance in the improvements seen in younger adults and only 3.2% of the variance in older adults. Changes in pupil size can improve the ability to filter noise, and these findings suggest that any changes in the spatial-frequency characteristics of the external noise due to changes in pupil size are likely to be only a small factor in the overall effect of learning in younger individuals and explain very little of the overall effect of learning in older subjects.

Contrast-Sensitivity and Acuity Analysis

Near-acuity, far-acuity, and contrast-sensitivity measurements were made before and after training. Contrast sensitivity was measured using the Pelli-Robson Test. One-tailed p values are reported for all measures. A single contrast-sensitivity measurement for 1 younger subject was lost and is missing from the analysis.

Figure 8:
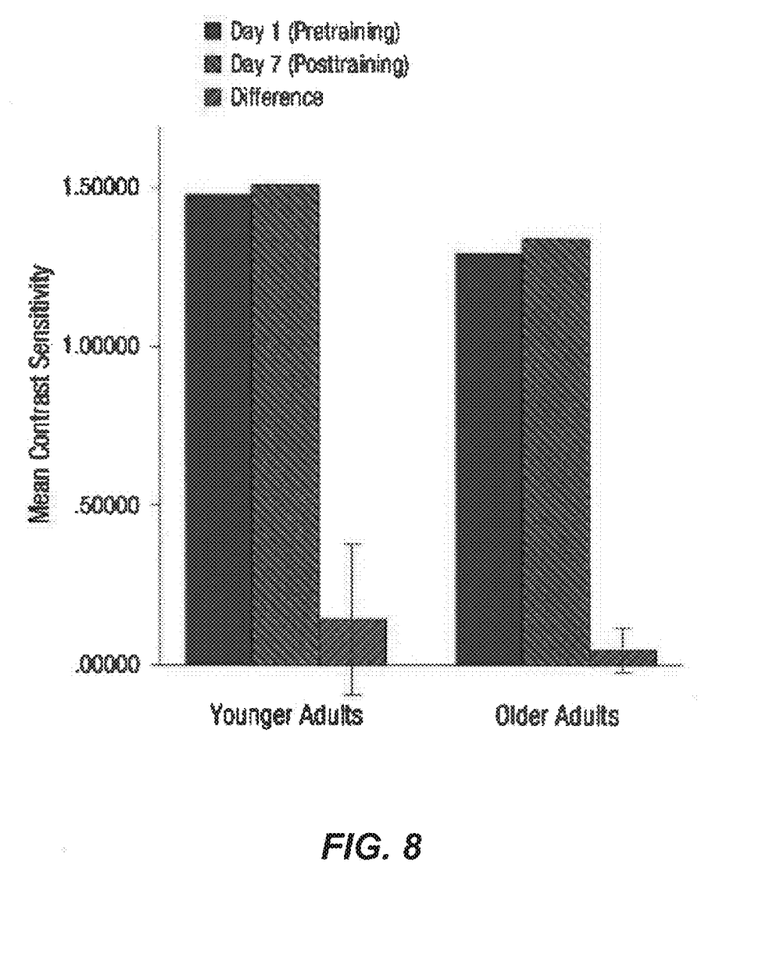
FIG. 8 is a graph of the Mean log contrast sensitivity as a function of age group and testing day.

Neither younger nor older individuals demonstrated any significant improvement in contrast sensitivity, $t(12)=-1.389$, $p=0.190$, and $d=-0.385$, $t(12)=-1.477$, $p=0.0825$, $d=0.410$, respectively. FIG. 8 is a graph of the Mean log contrast sensitivity as a function of age group and testing day. The difference between pre- and posttraining sensitivity is also shown. Error bars indicate 95% confidence intervals.

Figure 9:
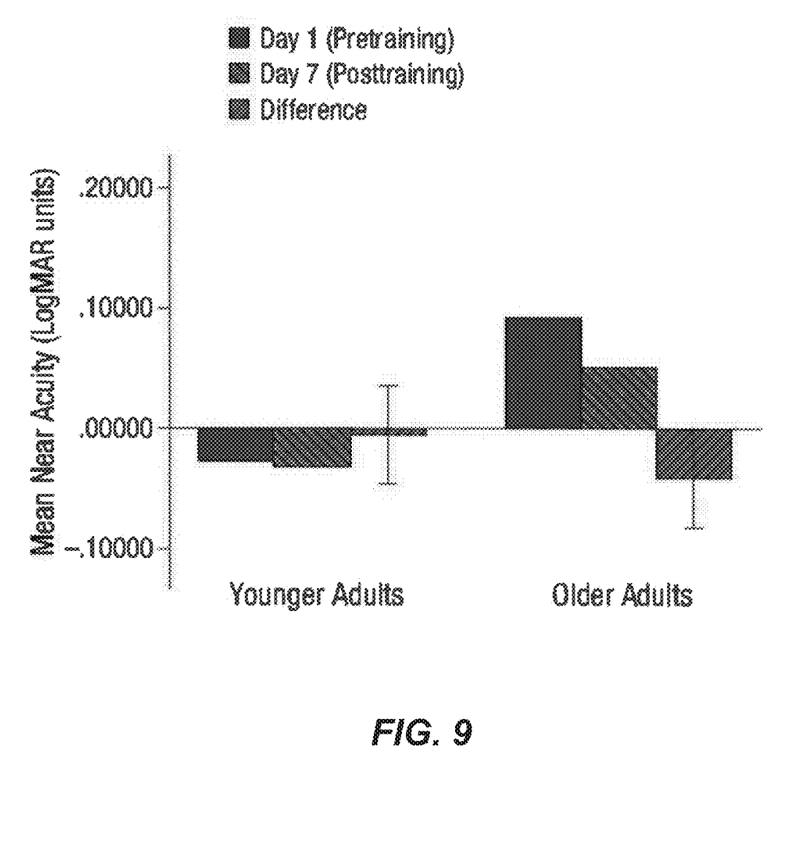
FIG. 9 is a graph of the mean near acuity as a function of age group and testing day.

To adjust for multiple comparisons when analyzing the acuity data, the Benjamini-Hochberg procedure was used to control the false discovery rate (FDR; Benjamini & Hochberg, 1995). Older individuals showed a significant improvement in near acuity, $t(12)=2.217$, $p_{FDR}=0.047$, $d=0.615$, whereas no significant change in near acuity was found in younger individuals, $t(13)=0.265$, $p_{FDR}=0.398$, $d=0.071$. FIG. 9 is a graph of the mean near acuity as a function of age group and testing day. The difference between pre- and posttraining acuity is also shown. Error bars indicate 95% confidence intervals. Log MAR=logarithm of the minimum angle of resolution.

Figure 10:
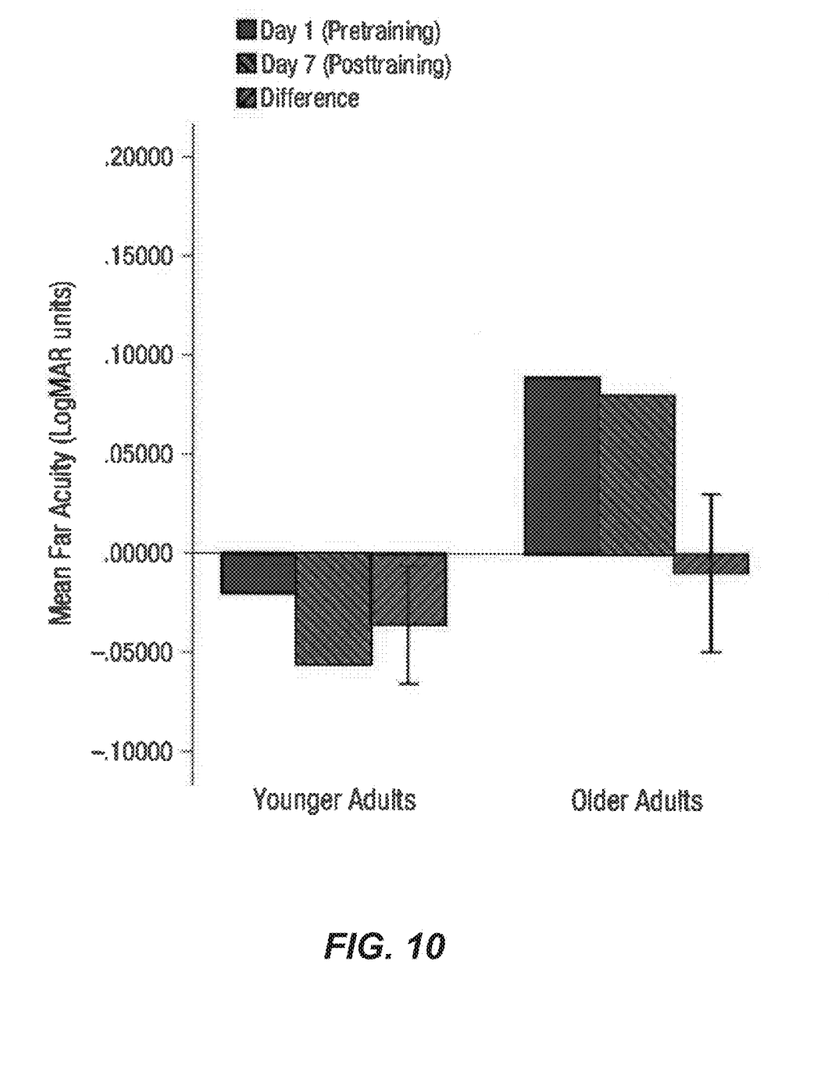
FIG. 10 is a graph of the mean far acuity as a function of age group and testing day.

Similarly, older individuals showed no significant change in far acuity, $t(12)=0.503$, $p_{FDR}=0.398$, $d=0.140$, whereas a significant improvement in far acuity was found for younger individuals, $t(13)=2.592$, $p_{FDR}=0.044$, $d=0.693$. FIG. 10 is a graph of the mean far acuity as a function of age group and testing day. The difference between pre- and posttraining acuity is also shown. Error bars indicate 95% confidence intervals. Log MAR=logarithm of the minimum angle of resolution.

Overall, these results are important for several reasons. First, contrast sensitivity can be improved for trained stimuli through behavioral training in both younger and older adults. The performance improvements for older adults are striking. Contrast-sensitivity thresholds for the highest-noise condition are the most difficult condition for both age groups. Prior to training, younger adults (mean threshold=0.25) had significantly lower thresholds than older adults (mean threshold=0.39) in the high-noise condition, $1(1, 25)=6.341$, $p<0.01$, $\eta_p^2=0.201$. However, an analysis comparing performance in the high-noise condition for younger adults before training (mean threshold=0.25) and older adults after training (mean threshold=0.26) was not significant, $1(1, 25)=0.152$, $p>0.05$, $\eta_p^2=0.006$. The change in the pattern of results is due to improved performance in older adults, as indicated by a significant effect of training for the high-noise condition (pretraining and posttraining thresholds=0.39 and 0.26, respectively), $1(1, 12)=10.215$, $p<0.01$, $\eta_p^2=0.460$.

Discussion

The system and method uses perceptual learning to improve older adults' ability to see low-contrast stimuli. In testing the system and method, 5 days of training for older adults resulted in performance that was not statistically different from that of younger adults prior to training. This finding indicates that perceptual learning can be used to counteract age-related declines in contrast sensitivity. These improvements are the result of changes in sensory processing and not due to optical efficiency of the eye.

A second important finding was that both younger and older individuals showed significant improvement in acuity with perceptual-learning training to improve contrast sensitivity. Notably, the improvements in acuity were associated with the range of acuity most problematic for each age group. Younger individuals tend to have near-optimal near acuity, as a result of a strong and fast accommodative response; they showed a significant change only in far acuity. Older individuals suffer from losses in near acuity, resulting from significant declines in the accommodative response. The improved performance in near acuity for older adults might be due to changes in improvements in the accommodative response. Previous research has found improved acuity after perceptual learning in middle-age adults (median=51 years) when declines in accommodative focus or presbyopia occur. However, unlike in the study described herein, in which there were 5 days of training, the training for middle-age adults occurred three times a week for 3 months over 36 training sessions. An important alternative embodiment would measure the accommodative focus response of older adults (i.e., over the age of 65 years) in response to training in contrast sensitivity.

A third finding was that both age groups showed significant transfer of learning to the untrained orientation. This transfer was more pronounced at higher noise levels. This is likely because the primary limiting factor for discrimination in high-noise cases is the external noise itself, not the contrast of the stimulus. This also suggests that filtering of external noise is not specific to the trained stimulus and may be a more general process that can transfer to a variety of tasks. One other possible explanation for the high degree of transfer is that the task used in the study was a fairly low-precision task. At high levels of contrast with no noise, subjects can perform the task using the system consistently with near-perfect accuracy, aside from any attentional lapses in their responses, as the task requires only coarse orientation discrimination with a constant 15° offset. High-precision tasks tend to show greater specificity than do low-precision tasks.

Finally, no significant correlation between a change in pupil size and improvement in the task was found for older individuals. However, a significant correlation was found in younger individuals, though this accounted for only around 5% of the variance. While it was proposed previously that older individuals may be compensating for a loss in retinal illuminance by dilating the pupils to allow more light to fall on the retina, the results from the retinal-illuminance data do not support this hypothesis. Given the small amount of variance explained by retinal illuminance in younger individuals, it is unlikely that this was a primary factor in the improvements seen in the task or the improvements seen in far acuity. It is intriguing that there was a significant change in retinal illuminance in younger adults; additional research will be needed to replicate this finding and determine the impact of this effect on training and improved vision.

In summary, the results of the actual embodiment tested indicate that perceptual learning may be a viable intervention for age-related declines in vision. The study performed using the system comprised only 5 days of training, whereas many perceptual-learning studies consist of much longer training periods, in some cases up to 30 days. Given the short training period, the degree of improvement is quite impressive, particularly in the cases of near and far acuity, in which subjects were able to read an average of two to three additional letters on acuity charts after training. Further study is needed to determine how much more improvement in near and far acuity may be obtained by older adults, as there was not a long enough training period in the study to determine whether asymptotic levels of performance were reached. However, the findings are quite promising and provide further evidence of the plasticity of visual processing in advanced age.

All features disclosed in the specification, including the claims, abstracts, and drawings, and all the steps in any method or process disclosed, may be combined in any combination, except combinations wherein at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function should not be interpreted as a "means" or "step" clause as specified in 35 U.S.C. § 112.

What is claimed is:

1. A computerized system for improving sight, comprising:
   a processor;
   a monitor;
   a first set of instructions executable on the processor configured to familiarize subjects with the system, said first set of instructions including:
      instructions for presenting a fixation point in the center of the monitor, alternating between black and white,
      instructions for presenting a Gabor patch on the monitor,
      instructions for presenting a second stimulus on the monitor,
      instructions for receiving input from the subjects on how the second stimulus is oriented;
   a second set of instructions executable on the processor configured for training the subjects, said second set of instructions including:
      instructions for presenting Gabor patches embedded in additive Gaussian noise on the monitor,
      instructions for increasing the standard deviation of the Gaussian distribution,
      instructions for receiving input from the subjects on how the Gabor patches are oriented; and
   wherein the first and second sets of instructions are further for presenting the Gabor patch at one of the two standard orientations for 100 and a second fixation point for 1,200 ms, alternating between black and white every 300 ms, followed by the target stimulus for 100 ms.

2. The system of claim 1, further comprising a means for measuring the size of the each subject's pupil size to derive retinal-illuminance values.

3. The system of claim 1, wherein the first and second sets of instructions are for causing the monitor to assume a uniform midgray value before receiving the input from the input from the subjects.

4. The system of claim 1, further comprising a keyboard with arrow keys to receive the input from the subjects.

5. The system of claim 1, wherein all stimuli are viewed through a circular annulus.

6. A method for improving sight, comprising:
   familiarizing subjects by:
      presenting a fixation point in the center of the monitor, alternating between black and white,
      presenting a Gabor patch on the monitor,
      presenting a second stimulus on the monitor,
      receiving input from the subjects on how the second stimulus is oriented;
   training the subjects by:
      presenting Gabor patches embedded in additive Gaussian noise on the monitor,
      increasing the standard deviation of the Gaussian distribution,
      receiving input from the subjects on how the Gabor patches are oriented; and
   presenting the Gabor patch at one of the two standard orientations for 100 and a second fixation point for 1,200 ms, alternating between black and white every 300 ms, followed by the target stimulus for 100 ms.

7. The method of claim 6, further comprising measuring the size of the each subject's pupil size to derive retinal-illuminance values.

8. The method of claim 6, further comprising causing the monitor to assume a uniform midgray value before receiving the input from the input from the subjects.

9. The method of claim 6, further comprising receiving the input from the subjects via arrows on a keyboard.

10. The method of claim 6, wherein all stimuli simuli are viewed through a circular annulus.

* * * * *